United States Patent
Dai et al.

(10) Patent No.: US 11,541,250 B2
(45) Date of Patent: Jan. 3, 2023

(54) INTRAOPERATIVE RADIATION THERAPY SYSTEM AND METHOD FOR INTRAOPERATIVE RADIATION THERAPY

(71) Applicant: Cancer Hospital, Chinese Academy of Medical Sciences, Beijing (CN)

(72) Inventors: Jianrong Dai, Beijing (CN); Pan Ma, Beijing (CN); Chuanmeng Niu, Beijing (CN); Minghui Li, Beijing (CN)

(73) Assignee: Cancer Hospital, Chinese Academy of Medical Sciences, Beijing (CN)

( * ) Notice: Subject to any disclaimer, the term of this patent is extended or adjusted under 35 U.S.C. 154(b) by 1046 days.

(21) Appl. No.: 15/978,449

(22) Filed: May 14, 2018

(65) Prior Publication Data
US 2019/0134424 A1 May 9, 2019

(30) Foreign Application Priority Data
May 15, 2017 (CN) .............................. 201710337491

(51) Int. Cl.
*A61N 5/10* (2006.01)

(52) U.S. Cl.
CPC ......... *A61N 5/1001* (2013.01); *A61N 5/1083* (2013.01); *A61N 5/1039* (2013.01); *A61N 5/1064* (2013.01); *A61N 5/1071* (2013.01); *A61N 2005/1074* (2013.01)

(58) Field of Classification Search
None
See application file for complete search history.

(56) References Cited

U.S. PATENT DOCUMENTS

| | | | |
|---|---|---|---|
| 5,321,271 A | 6/1994 | Schonberg | |
| 5,635,721 A | 6/1997 | Bardi | |
| 6,610,013 B1 * | 8/2003 | Fenster | A61N 5/103 600/439 |
| 10,603,010 B2 * | 3/2020 | Kelly | A61B 8/4218 |
| 2004/0260142 A1 * | 12/2004 | Lovoi | A61N 5/1015 600/1 |
| 2009/0024030 A1 | 1/2009 | Lachaine | |

(Continued)

FOREIGN PATENT DOCUMENTS

| CN | 1537657 A | 10/2004 |
|---|---|---|
| CN | 104884126 A | 9/2015 |

(Continued)

OTHER PUBLICATIONS

De Jean et al. (2009). Three-dimensional ultrasound system for guided breast brachytherapy. Med. Phys., 36(11). doi: 10.1118/1. 3243865 (Year: 2009).*

(Continued)

*Primary Examiner* — Angela M Hoffa
*Assistant Examiner* — Younhee Choi
(74) *Attorney, Agent, or Firm* — Radlo & Su

(57) ABSTRACT

A method for planning a scan path for intraoperative radiation therapy may comprise acquiring a plurality of images of a region of interest through an auxiliary scanning component, establishing a 3D model of the region of interest based on the plurality of images of the region of interest, determining a radiation therapy volume based on the 3D model of the region of interest, and planning a scan path for a radiation therapy component to scan the radiation therapy volume.

6 Claims, 4 Drawing Sheets

(56) References Cited

U.S. PATENT DOCUMENTS

| | | | |
|---|---|---|---|
| 2009/0299175 A1* | 12/2009 | Bernstein | A61B 5/0507 600/425 |
| 2010/0034357 A1* | 2/2010 | Svesson | A61N 5/1042 378/152 |
| 2010/0063396 A1* | 3/2010 | Anderson | A61B 8/462 600/459 |
| 2011/0052036 A1* | 3/2011 | Valdivieso Cacique | A61N 5/1031 703/11 |
| 2012/0035462 A1* | 2/2012 | Maurer, Jr. | A61N 5/1077 600/411 |
| 2012/0234625 A1* | 9/2012 | Laugharn, Jr. | G10K 11/28 181/140 |
| 2013/0116570 A1* | 5/2013 | Carson | A61B 6/502 600/459 |
| 2015/0306423 A1 | 10/2015 | Bharat | |
| 2016/0089549 A1 | 3/2016 | Ranganathan | |
| 2016/0271422 A1 | 9/2016 | Gemmel | |
| 2017/0128042 A1* | 5/2017 | Desai | A61B 8/4422 |
| 2018/0015303 A1* | 1/2018 | Fishman | A61B 34/20 |

FOREIGN PATENT DOCUMENTS

| | | |
|---|---|---|
| CN | 104902957 A | 9/2015 |
| CN | 105377368 A | 3/2016 |
| CN | 105879244 A | 8/2016 |
| WO | WO2015127970 A1 | 3/2015 |

OTHER PUBLICATIONS

Poulin et al. (2015). A novel robot-assisted 3DUS system. Med. Phys, 42(12). doi: 10.1118/1.4934832. (Year: 2015).*

Search Report by the National Intellectual Property Administration, PRC (China Patent Office) dated Feb. 25, 2019.

Notice of Allowance, National Intellectual Property Administration, PRC (China Patent Office), dated Oct. 25, 2019.

English Translation of the Abstract, CN105879244A.

English Translation of the Abstract, CN1537657A.

* cited by examiner

INTRAOPERATIVE RADIATION THERAPY SYSTEM AND METHOD FOR INTRAOPERATIVE RADIATION THERAPY

CROSS REFERENCE TO RELATED APPLICATIONS

The present invention generally relates to the field of medical radiation therapy, and more particularly, to an intraoperative radiation therapy system and a method for the intraoperative radiation therapy.

TECHNICAL FIELD

The present invention generally relates to the field of medical radiation therapy, and more particularly, to an intraoperative radiation therapy system and a method for planning a scan path for the intraoperative radiation therapy.

BACKGROUND

Intraoperative radiation therapy (IORT) is a technology that applies a high level of radiation directly to a tumor, a tumor bed, or a recrudesce or metastasis region visible during surgery. An advantage of the technology is that important organs adjacent to the target (i.e., the to-be-irradiated area) of the patient may be pushed out of the irradiation field in the surgery so as to reduce the radiation dose applied thereto.

In the late 1990s, Hitesys S.P.A. in Italy firstly launched a mobile IORT apparatus NOVAC7, details of which are described in a U.S. Pat. No. 5,635,721. Then, Intraop Medical Inc. in the United States launched another mobile electron linear accelerator MOBETRON dedicated for an IORT apparatus, which is detailed in a U.S. Pat. No. 5,321,271. However, neither of the two apparatuses uses intraoperative radiation therapy images, and it entirely relies on experience and skills of clinicians to perform the intraoperative radiation therapy, which may cause the radiation dose insufficient for the target area or excessive for surrounding important organs and thus cannot achieve a desirable effect of the intraoperative radiation therapy.

A Chinese patent No. ZL200310108091.2 entitled "APPARATUS FOR INTRAOPERATIVE RADIATION THERAPY" discloses a new apparatus for intraoperative radiation therapy. The apparatus uses CT and MRI 3D images to determine direction and position of an electron beam incident onto a lesion. The electron linear accelerator is fixed to the ceiling of the operation room through a motion frame, and it may be placed at a predetermined position for intraoperative radiation therapy by moving the motion frame and an operation table. Although the apparatus utilizes 3D images, the images are acquired by CT or MRI devices before the surgery, and it cannot determine a relationship between the lesion and normal tissues and important organs in a condition where the tumor bed is exposed, and thus cannot obtain an optimum treatment solution.

At present, an IORT treatment scheme is determined by a radiation oncologist based on her/his experience within a short time when she/he comes to the operation table. Due to lack of 3D intraoperative images and dose distribution information, a 3D dose distribution of the radiation irradiated on the tissues cannot be evaluated, and whether or not treatment parameters (e.g., size, angle of a treatment applicator, beam energy) in the treatment scheme can be correctly selected depends largely on experience of the radiation oncologist. As a result, insufficient dose in the target area or excessive dose to the important organs may occur, which impacts the effect of the IORT treatment.

Further, a lot of time-costing preparation work is required before the IORT treatment starts. For example, the radiation oncologist needs to manually place and fix the treatment applicator and manually control a handle to move the head of the electron accelerator so that a central axis of the electron beam is aligned to a central axis of the applicator. Therefore, it is difficult to ensure precision of the irradiation. In addition, the radiation therapy is performed simply with a single energy in a fixed irradiation field, and the electron beam with the single energy can irradiate only to a single depth, which can not completely accommodate the spatial shape of the tumor with varying depth and thus normal tissues surrounding the tumor cannot be protected from radiation.

SUMMARY

In order to address one or more deficiencies of the prior arts, the present invention provides a method for planning a scan path for intraoperative radiation therapy, an intraoperative radiation therapy system and its control device, which establish a 3D model of an area of interest based on intraoperative images so as to precisely determine a radiation therapy volume and deliver radiation dose for the determined radiation therapy volume. In the present application, a robotic arm may be used to implement mechanical scanning of an intraoperative radiation therapy component with high precision and multiple degree-of-freedom (DOF) so as to accomplish a precise intensity-modulated and energy-modulated radiation therapy treatment. Using of the robotic arm may also help to establish a unified coordinate system for the intraoperative radiation therapy in a complex environment of the operation room so that a spatial position relationship between simulation positioning and treatment implementation may be determined.

According to an exemplary embodiment of the present invention, a method for planning a scan path for intraoperative radiation therapy may comprise acquiring a plurality of images of an area of interest through an auxiliary scanning component, establishing a 3D model of the area of interest based on the plurality of images of the area of interest, determining a radiation therapy volume based on the 3D model of the area of interest, and planning a scan path for a radiation therapy component to scan the radiation therapy volume.

In some embodiments, the auxiliary scanning component may comprise an applicator having an open upper end and a closed bottom, and the applicator may be set up so that the closed bottom attaches to the area of interest.

In some embodiments, acquiring a plurality of images of an area of interest through an auxiliary scanning component may comprise using an ultrasonic device, a CT device, an X-ray device, or a MRI device to acquire the plurality of images of the area of interest.

In some embodiments, acquiring a plurality of images of a region of interest through an auxiliary scanning component may comprise manipulating an ultrasonic device by a robotic arm to scan on the inner bottom surface of the auxiliary scanning component so as to acquire the plurality of images of the region of interest.

In some embodiments, determining a radiation therapy volume based on the 3D model of the region of interest may comprise recognizing the radiation therapy volume in the 3D model directly by an image recognition module, or receiving selection of the radiation therapy volume in the 3D model from a user, or preliminarily recognizing the radiation therapy volume in the 3D model by an image recognition module and then receiving modification of a user to the radiation therapy volume preliminarily recognized by the image recognition module so as to eventually determine the radiation therapy volume.

In some embodiments, planning a scan path for a radiation therapy component in the radiation therapy volume may comprise dividing the radiation therapy volume into a plurality of sub-volumes, determining a radiation dose for each sub-volume, and planning a scan path and a scan mode for the radiation therapy component to scan each of the sub-volume in intensity-modulated and energy-modulated manner where the scan mode includes a stepping scan mode and a dynamically continuous scan mode.

According to an exemplary embodiment of the present invention, an intraoperative radiation therapy control device may comprise an imaging control module for controlling an imaging component to move along a predetermined path and scan a region of interest through an auxiliary scanning component so as to acquire a plurality of images of the region of interest, a modeling module for establishing a 3D model of the region of interest based on the plurality of images of the region of interest, a radiation therapy volume determination module for determining a radiation therapy volume in the 3D model of the region of interest, and a radiation therapy path planning module for planning a path along which a radiation therapy component scans the radiation therapy volume.

In some embodiments, the intraoperative radiation therapy control device may further comprise a radiation therapy execution module for controlling a robotic arm to move the radiation therapy component along the planned path to perform the radiation therapy.

In some embodiments, the auxiliary scanning component may comprise an applicator with an open upper end and a closed bottom, and the applicator may be set up so that the closed bottom attaches to the region of interest.

In some embodiments, the imaging control module may be configured to control an ultrasonic device, a CT device, an X-ray device, or a MRI device to scan the region of interest to acquire the plurality of images of the region of interest.

In some embodiments, the imaging component may comprises an ultrasonic device, and the imaging control module may be configured to control a robotic arm to manipulate the ultrasonic device to scan the region of interest so as to acquire the plurality of images of the region of interest.

In some embodiments, the imaging control module may be further configured to plan the predetermined path based on information of the auxiliary scanning component and the ultrasonic device before it controls the robotic arm to manipulate the ultrasonic device.

In some embodiments, the radiation therapy volume determination module may comprise an image recognition unit configured to recognize the radiation therapy volume in the 3D model, and a radiation therapy volume selection unit configured to receive selection of the radiation therapy volume in the 3D model from a user.

In some embodiments, the radiation therapy path planning module may comprise a sub-volume dividing unit configured to divide the radiation therapy volume into a plurality of sub-volumes, a radiation dose determining unit configured to determine a radiation dose for each of the sub-volumes, and a radiation therapy path planning unit configured to plan a scan path and a scan mode for the radiation therapy component to scan each of the sub-volumes in an intensity-modulated and energy-modulated manner where the scan mode includes a stepping scan mode and a dynamically continuous scan mode.

In some embodiments, the radiation therapy execution module may comprise a robotic arm control unit configured to control the robotic arm to move the radiation therapy component along the planned path to perform the radiation therapy, and a radiation therapy component control unit configured to control radiation intensity and energy of the radiation therapy component while the radiation therapy component is moving.

According to an exemplary embodiment of the present invention, an intraoperative radiation therapy system may comprise an auxiliary scanning component, an imaging component, a radiation therapy component, a robotic arm and a control component including a memory having computer instructions stored thereon and a processor configured to execute the computer instructions so as to perform the following steps: controlling the imaging component to scan a region of interest through the auxiliary scanning component placed on the region of interest to acquire a plurality of images of the region of interest, establishing a 3D model of the region of interest based on the plurality of images of the region of interest, determining a radiation therapy volume based on the 3D model, planning a path along which the radiation therapy component scans the radiation therapy volume, and controlling the robotic arm to move the radiation therapy component along the planned path to perform radiation therapy on the radiation therapy volume.

In some embodiments, the auxiliary scanning component may comprise an applicator with an open upper end and a closed bottom, and the applicator may be set up so that the closed bottom attaches to the region of interest.

In some embodiments, the imaging component may comprise an ultrasonic device, a CT device, an X-ray device, or a MRI device.

In some embodiments, the imaging component may comprise an ultrasonic device, and the ultrasonic device is moved by the robotic arm on the inner bottom surface of the auxiliary scanning component so as to acquire the plurality of images of the region of interest.

In some embodiments, determining a radiation therapy volume based on the 3D model may comprise: recognizing the radiation therapy volume in the 3D model directly by image recognition; or receiving selection of the radiation therapy volume in the 3D model from a user; or preliminarily recognizing the radiation therapy volume in the 3D model by image recognition, and then receiving modification of the preliminarily recognized radiation therapy volume from the user so as to finally determine the radiation therapy volume.

In some embodiments, planning a path along which the radiation therapy component scans the radiation therapy volume may comprise dividing the radiation therapy volume into a plurality of sub-volumes, determining a radiation dose for each of the sub-volumes, and planning a scan path and a scan mode for the radiation therapy component to scan each of the sub-volumes in an intensity-modulated and energy-modulated manner where the scan mode includes a stepping scan mode and a dynamically continuous scan mode.

According to an exemplary embodiment of the present invention, a computer-readable storage medium may have computer program instructions stored thereon, the computer program instructions may configure a processor to perform the above-mentioned methods when they are executed in the processor.

In some embodiments, the computer program instructions may configure the processor to perform the following step when they are executed in the processor: controlling the robotic arm to move the radiation therapy component along the planned path to perform radiation therapy on the radiation therapy volume.

The present invention has the following beneficial effects: the IORT robotic arm scanning method may implement mechanical scanning with multiple degree-of-freedom (DOF) and high precision, and using of the robotic arm may help to establish a unified coordinate system for the intraoperative radiation therapy in a complex environment of the operation room so that a spatial position relationship between simulation positioning and treatment implementation may be determined. The robotic arm may hold the ultrasonic component and implement intraoperative 3D ultrasonic image acquisition using automatic control technologies. The ultrasonic imaging has advantages of no radiation, high resolution to soft tissue, small size, low cost and the like, and the intraoperative 3D images may help to precisely determine the radiation therapy volume. The robotic arm may also hold the treatment component and implements intraoperative 3D intensity-modulated and energy-modulated treatment using the automatic control technologies, which may ensure the prescribed radiation dose in the target volume and effectively protect the normal tissues, thereby meeting requirements of precise IORT treatment.

BRIEF DESCRIPTION OF THE DRAWINGS

Various aspects of at least one embodiment are discussed below with reference to the accompanying drawings, which are not intended to be drawn to scale. The drawings are included to provide illustration and a further understanding of the various aspects and embodiments, and are incorporated in and constitute a part of this specification, but are not intended as a definition of the limits of the invention. In the drawings.

DESCRIPTION OF EMBODIMENTS

Hereinafter the present invention will be described in more detail with reference to the drawings in order to make the technical solutions, creative features, achievements and effects of the present invention easy to understand.

Figure 1:
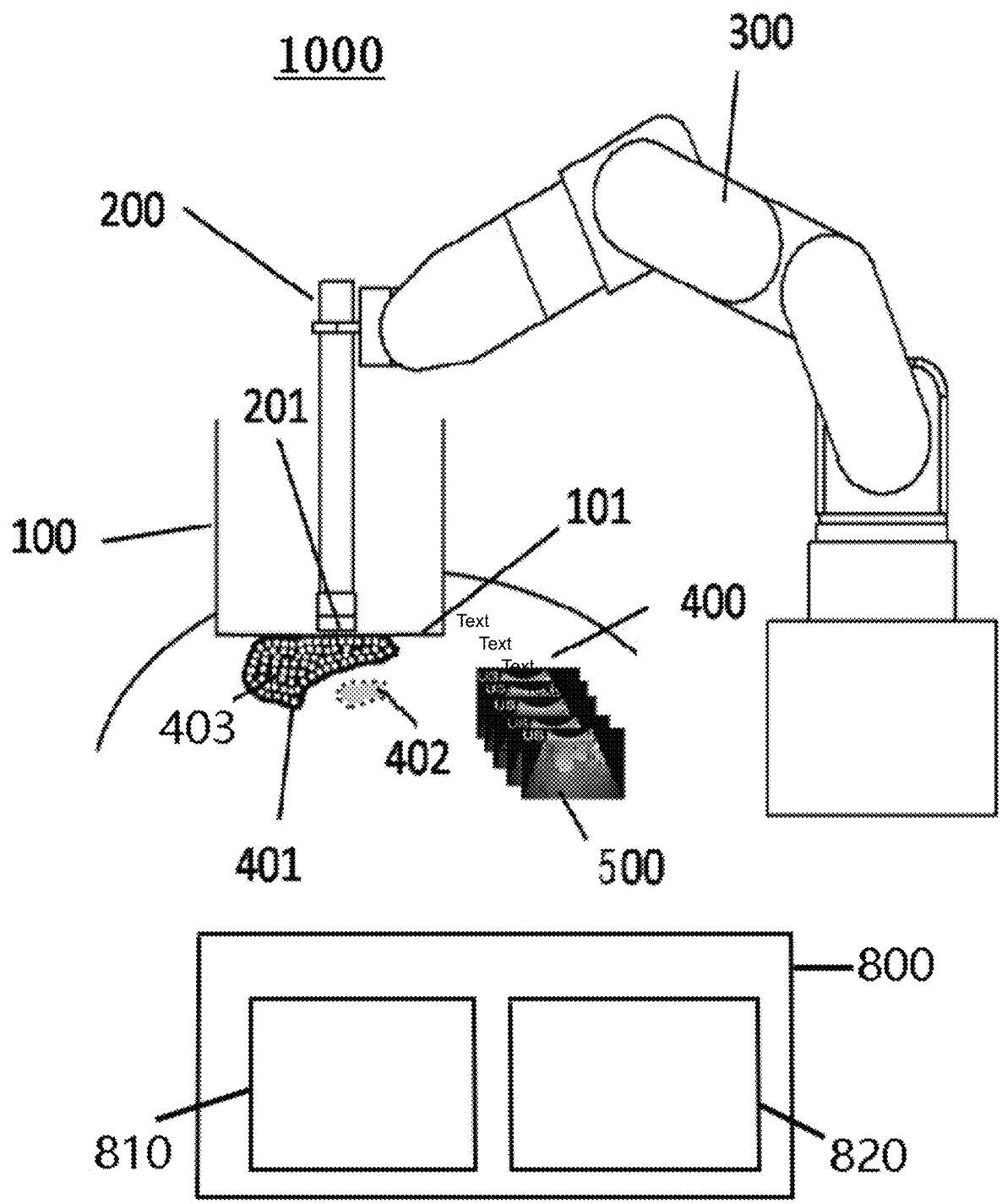
FIG. 1 is a schematic diagram showing an intraoperative radiation therapy system that is implementing intraoperative radiation therapy scan path planning according to an embodiment of the present invention.

FIG. 1 is a schematic diagram showing an intraoperative radiation therapy system 1000 that is implementing intraoperative radiation therapy scan path planning according to an embodiment of the present invention. As shown in FIG. 1, the intraoperative radiation therapy system 1000 may include an auxiliary scanning component 100, an imaging component 200, a robotic arm 300, and a control component 800 for controlling of the intraoperative radiation therapy system 1000. In addition, the intraoperative radiation therapy system 1000 may further include a radiation therapy component 600 (or 700 in FIG. 3), which will be described in more detail later.

The auxiliary scanning component 100 may have a cylinder shape to define a region for ultrasound scan, and it may also have other shapes such as rectangular, square, or the like. For example, the auxiliary scanning component 100 may be a multifunctional applicator that has an open upper end and a closed bottom 101. The closed bottom 101 may have a flat shape, or an arc shape that accommodates an imaging end surface of the imaging component 200. The bottom 101 is preferably formed of a material that an imaging beam and a radiation beam may easily pass through, and examples of the material may include but not limited to polyurethane and the like. Other aspects of the multifunctional applicator have already been described in detail in Chinese patent application No. 201610207427.8 published on Aug. 24, 2016, so a repetitive description thereof will be omitted here.

As shown in FIG. 1, the auxiliary scanning component 100 (i.e., the multifunctional applicator) may be placed on a region of interest of a patient 400. It should be noted that the placement of the auxiliary scanning component 100 is implemented during surgery, for example, after resection of a tumor, so that the outer surface of the bottom 101 of the auxiliary scanning component 100 may directly and closely attach to the region of interest (for example, a tumor bed). For example, the outer surface of the bottom 101 may be directly placed on the residual tumor or tumor bed 401, which may produce several beneficial effects. Firstly, as it is performed during surgery, the imaging component may be placed closer to the region of interest so as to acquire more clear and accurate images of the region of interest. Secondly, when the auxiliary scanning component 100 closely attaches to the region of interest, position of the region of interest may be fixed relative to the auxiliary scanning component 100, so as to avoid unfavorable influence on the image acquisition and subsequent radiation therapy due to movement of the region of interest.

After the auxiliary scanning component 100 is set up, the intraoperative radiation therapy system 1000 may, under control of the control component 800, implement various functional operations such as planning a scan path for the intraoperative radiation therapy and the intraoperative radiation therapy as described in detail later. The control component 800 may be a dedicated control device that includes hardware dedicated to controlling of the intraoperative radiation therapy system 1000, and it may also be a general computer such as a desktop computer, a laptop computer, a tablet computer, or even a mobile phone, which executes computer instructions to control various operations of the intraoperative radiation therapy system 1000.

Generally, the control component 800 may include a memory 810 and a processor 820. The memory 810 may include various computer-readable storage mediums such as ROM, RAM, EEPROM, magnetic disks, optical disks, floppy disks, flash memory, and the like. The memory 810 may have computer program instructions stored therein, and the processor 820 may execute the computer program instructions so as to implement various operations that will be described in detail below. The memory 810 may also store other data such as information of the intraoperative radiation therapy system, parameters of various components thereof, user information, patient information, and the like.

The processor 820 may be a central processing unit (CPU) or other processing units having data processing capabilities and/or instruction execution capabilities, and it may control other components of the intraoperative radiation therapy system 1000 to implement desirable functions. Although FIG. 1 shows one memory 810 and one processor 820, the control component 800 may include a plurality of memories 810 and a plurality of processors 820, and such memories and processors may be distributed at different locations, for example, a processor and a memory located on or near the robotic arm 300 for controlling the robotic arm, a processor and a memory located in the imaging component 200 for controlling the imaging component 200, and a processor and a memory located in the radiation therapy component 600 or 700 for controlling the radiation therapy component 600 or 700, and the like. In this regard, the memory and the processor are not limited in any way in the present invention as long as they are capable of implementing various functions described below.

Although it is not shown, the control component 800 may also have various interfaces, for example, interfaces for connection with components of the intraoperative radiation therapy system 1000, interfaces for connection with input devices such as keyboard, mouse, microphone or the like, and interfaces for connection with output devices as display, printer, speaker or the like. The control component 800 may also have a network interface through which it may be connected to a hospital information system (HIS) or the internet. It is apparent for those skilled in the art that many functions of the intraoperative radiation therapy system 1000 may be implemented by means of these interfaces.

Figure 2:
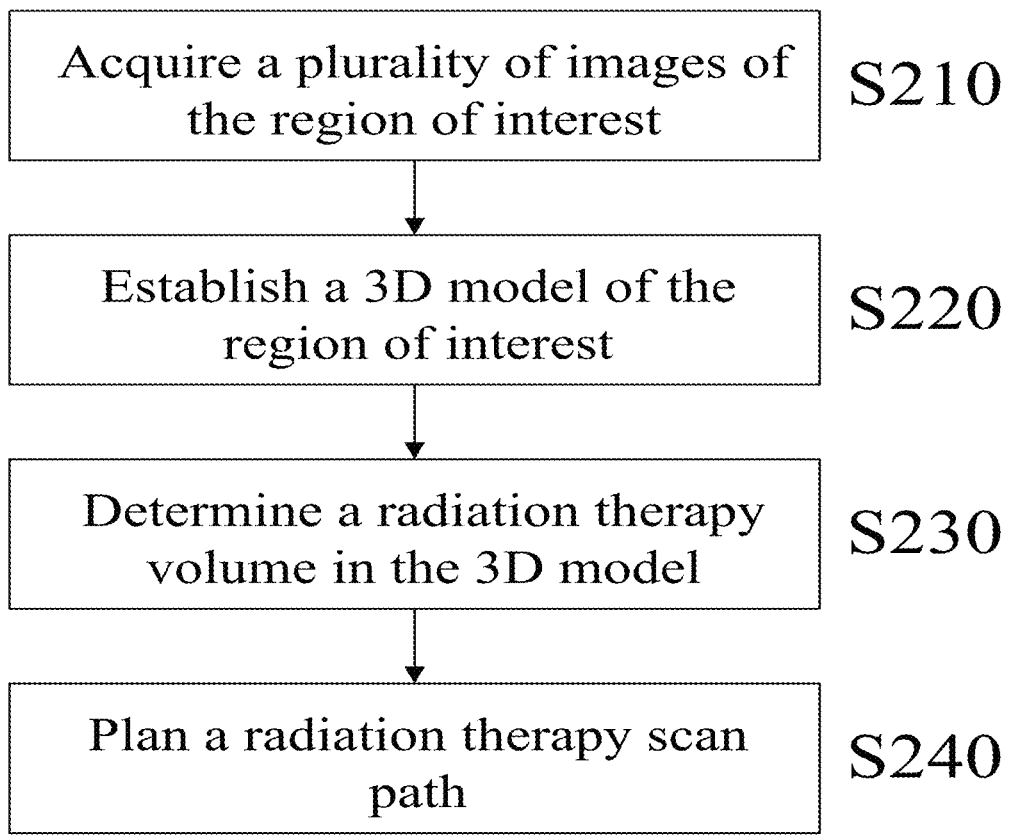
FIG. 2 is a flow chart showing a method for planning a scan path for intraoperative radiation therapy according to an embodiment of the present invention.

FIG. 2 is a flow chart showing a method for planning a scan path for intraoperative radiation therapy according to an embodiment of the present invention. Hereinafter, the method for planning a scan path for intraoperative radiation therapy will be described with reference to FIG. 1 and FIG. 2.

Firstly, at a step S210, the imaging component 200 is used to acquire a plurality of images of the region of interest through the auxiliary scanning component 100 which is set up on the region of interest as shown in FIG. 1. The imaging component 200 may be an imaging component commonly used in hospitals, such as an ultrasonic device, a CT device, an X-ray device, an MRI device, or the like. As the present application relates to intraoperative radiation therapy, these imaging components need to be provided in the operation room. For the sake of convenience, the ultrasonic component is preferred. The following description will be made with the ultrasonic component 200 as an example, but it should be understood under the teaching of the present invention that the image acquisition process may also be implemented by other imaging components.

As shown in FIG. 1, the ultrasonic component 200 may be installed at the end of the robotic arm 300. The ultrasonic component 200 may be installed manually by a user, or the robotic arm 300 may, under control of the control component 800, actively grip the ultrasonic component 200 that is placed at a predetermined position. The ultrasonic component 200 and the end of the robotic arm 300 may be provided with engagement features that match each other, such as corresponding bulge and depression, so that the ultrasonic component 200 is installed in a fixed position on the end of the robotic arm 300. Then, the ultrasonic component 200 installed on the robotic arm 300 may be moved to a center position of the auxiliary scanning component 100, and an end 201 of the ultrasonic component 200 may closely attach to the inner bottom surface of the auxiliary scanning component 100. As described above, the bottom of the auxiliary scanning component 100 may have an arc shape or a flat shape that accommodates the shape of the end of the ultrasonic component 200 so as to improve image quality.

At this point, position parameters of the robotic arm 300 may be initialized so that the current position of the robotic arm is considered as a reference position, i.e., an origin of a coordinate system, which is convenient for subsequent scanning motion of the robotic arm. Information of the auxiliary scanning component 100 such as outer diameter, inner diameter, and material and thickness of the bottom 101, and information of the ultrasound component 200 such as outer diameter, initial position may be stored in the memory 810. Thus, the control component 800 may use such information to make a plan for an imaging scan path of the robotic arm 300 and to determine control parameters of the ultrasonic component 200.

Then, the control component 800 may control the robotic arm 300 to move the ultrasonic component 200 along the planned imaging scan path and control the ultrasonic component 200 based on the determined control parameters so as to acquire a plurality of images of the region of interest, such as images 500 shown in FIG. 1. The ultrasound component 200 may be a 2D ultrasonic component or a 3D ultrasonic component, and thus the acquired images may be 2D images or 3D images. The ultrasonic component 200 may include a multi-frequency detector, such as a single multi-frequency ultrasonic detector or a combination of multiple single-frequency ultrasonic detectors of different frequencies, so as to acquire images of different frequencies, which may increase imaging depth.

The acquired images may be stored in for example the memory 810, and the control component 800 may establish a 3D model of the region of interest based on the images, thereby completing the step S220.

Next, in a step S230, a radiation therapy volume may be determined based on the 3D model of the region of interest. The radiation therapy volume may be a 3D volume such as a stereoscopic residual tumor, a tissue and the like, or it may be substantially a 2D region such as a tumor bed and the like. The radiation therapy volume may be determined in several ways. For example, image recognition technologies may be used to directly recognize a tumor volume in the 3D model as the radiation therapy volume. Alternatively, a user may use a mouse to select a particular region in the 3D model as the radiation therapy volume. In some embodiments, a combination of the two ways may be adopted. For example, the image recognition technologies may be used firstly to recognize an initial radiation therapy volume in the 3D model, and then the user may modify the initial radiation therapy volume to determine a final radiation therapy volume. In this way, both efficiency and precision may be ensured. With the 3D model, the determined radiation therapy volume may be conformal, for example, the volume 401 shown in FIG. 1, and normal tissues 402 below the volume 401 may be prevented from being included in the determined radiation therapy volume.

Then, in a step S240, a scan path may be planned for a radiation therapy component to scan the determined radiation therapy volume. More specifically, the radiation therapy scan path may be planned by the following process.

Firstly, relevant information of the radiation therapy component, such as an applicator 600 or an electron accelerator 700, has been stored in the memory 810, which may include for example spot size or diameter, intensity, intensity modulation precision, energy, energy modulation precision of the radiation beam. In view of parameters of the radiation therapy component 600, the radiation therapy volume 401 may be divided into a number of sub-volumes or blocks as shown by points 403 in the figure. It would be understood that if the radiation beam has a smaller diameter, intensity and energy modulation of the beam would have a higher precision, and thus the sub-volumes 403 may be smaller, and the number of the sub-volumes 403 may be greater.

Then, a radiation dose may be assigned to each of the sub-volumes. At this time, the sub-volumes 403 may be assigned with the same dose or different doses. For example, the user may select all or a part of the sub-volumes 403 and specify a dose value for the selected sub-volumes 403. In this way, different parts of the radiation therapy volume 401 may be flexibly assigned with different radiation dose values. For example, a smaller dose may be assigned to a part of the sub-volumes 403 adjacent to the normal tissues 402 to avoid possible damage to the normal tissues 402.

Finally, a radiation therapy scan path may be planned for the radiation therapy component 600 to scan each sub-volume 403. At this point, the scan path and scan mode may be determined for the radiation therapy component 600 to scan the sub-volumes 403 in an intensity-modulated and energy-modulated manner. It would be understood that energy of the radiation beam corresponds to depth of the radiation therapy, and the higher the energy, the greater the radiation therapy depth. Once the intensity and energy are determined, the radiation dose for each sub-volume 403 may be determined. The scan mode may include a stepping scan mode and a dynamically continuous scan mode. It should be noted that attenuation and absorption of the beam due to material and thickness of the bottom 101 of the auxiliary scan component 100 should also be considered in determining the intensity and energy of the beam.

Although it is not shown, the planned scan path may optionally be evaluated. For example, the radiation dose received by normal tissues may be assessed. If the radiation dose received by the normal tissues is lower than a threshold value, the planned path is considered acceptable and it may be output or saved; on the contrary, if the radiation dose received by the normal tissues is higher than the threshold value, the planned path is considered unacceptable and it needs to be adjusted until it meets the evaluation requirement.

Figure 3:
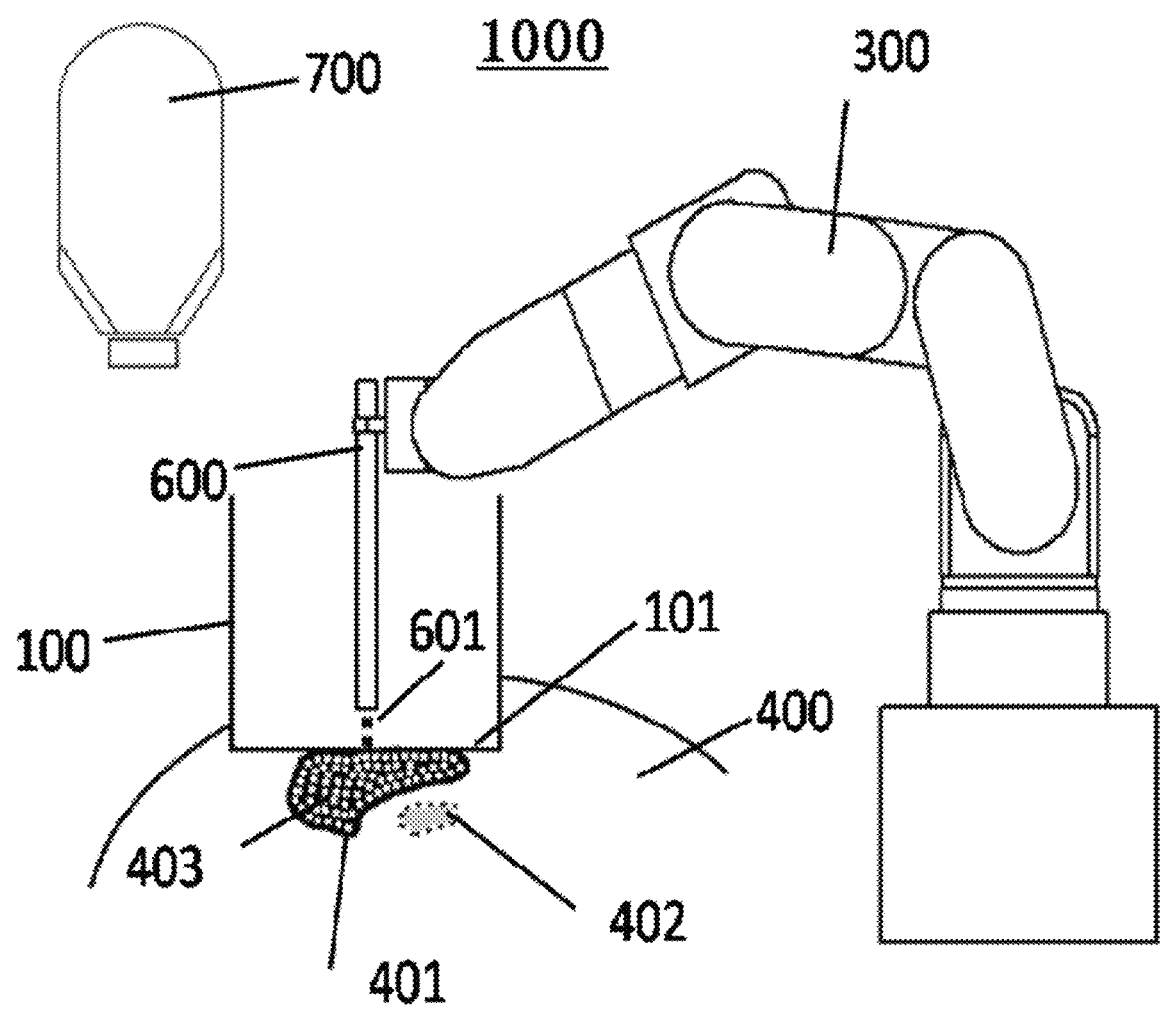
FIG. 3 is a schematic diagram showing an intraoperative radiation therapy system that is implementing intraoperative radiation therapy according to an embodiment of the present invention.

In this way, the plan of the radiation therapy scan path may be successfully established. Next, the planned radiation therapy scan path may be used to perform the radiation therapy, as shown in FIG. 3. Referring to FIG. 3, the radiation therapy applicator 600 may be mounted as the radiation therapy component on the robotic arm 300, and a radiation beam 601 may be directed through the applicator 600 to the points 403 in the radiation therapy volume 401. In some embodiments, other radiation therapy components such as the electron accelerator 700 may also be used.

It is noted that the auxiliary scan component 100 still remains closely attaching to the radiation therapy volume while performing the radiation therapy, which may bring several advantages. For example, the radiation therapy volume may be maintained in a fixed position relative to the auxiliary scanning component 100. As both the imaging component 200 and the radiation therapy component 600 may be positioned relative to the auxiliary scanning component 100, the radiation therapy volume is in the same position relative to the imaging component 200 and the radiation therapy component 600. Furthermore, the auxiliary scanning component 100 may help to establish the same coordinate system for both the imaging component 200 and the radiation therapy component 600. All of these advantages help to improve precision of the radiation therapy.

The control component 800 may control the robotic arm 300 and the radiation therapy component 600 installed thereon, according to the planned radiation therapy scan path including intensity, energy, scan mode and the like, to perform intensity-modulated and energy-modulated radiation therapy on the radiation therapy volume 401 that has an irregular shape, thereby forming a conformal dose distribution and effectively protecting the normal tissues 402 under the tumor or tumor bed.

Figure 4:
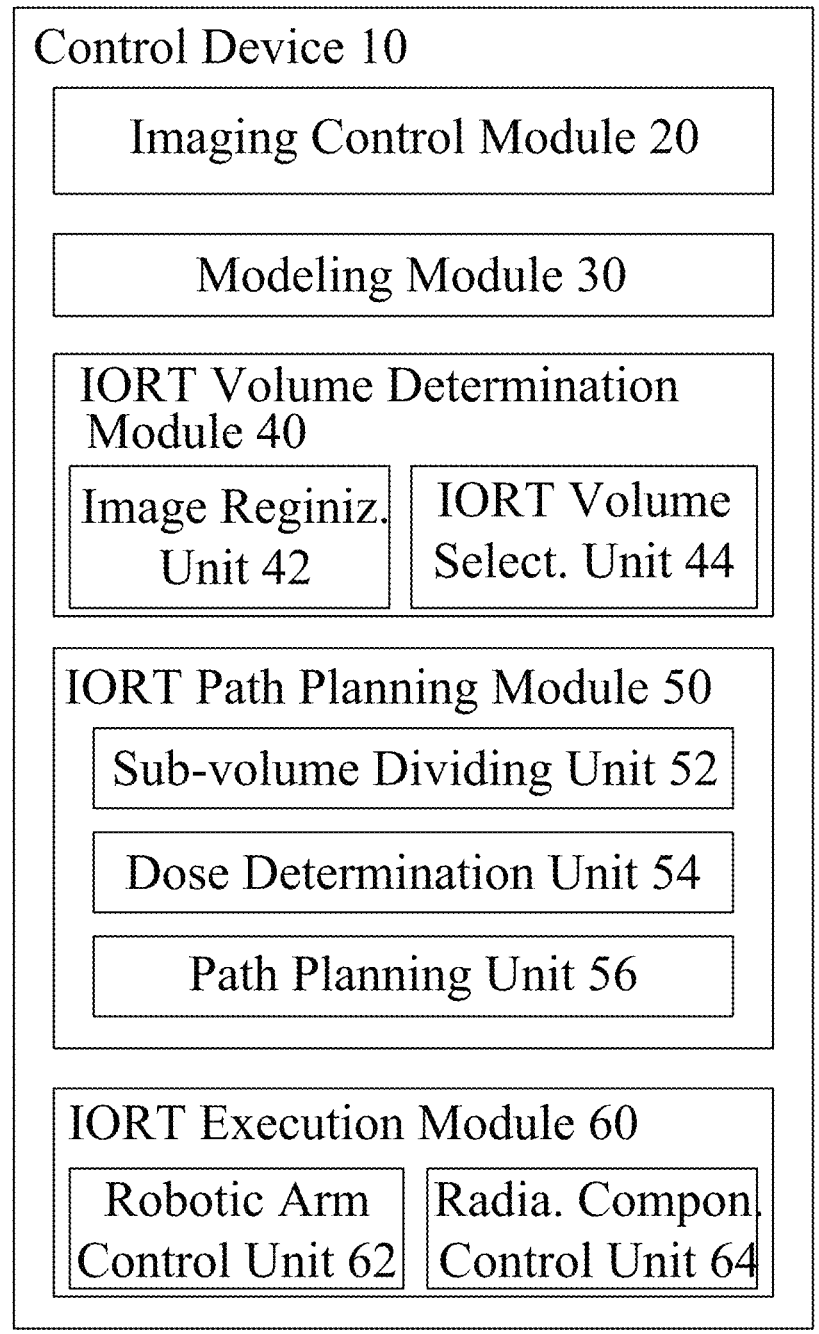
FIG. 4 is a block diagram showing a control device for the intraoperative radiation therapy system according to an embodiment of the present invention.

FIG. 4 is a block diagram showing a control device 10 that may be used in the aforementioned intraoperative radiation therapy system 1000 to perform the aforementioned operations or implement the aforementioned functions. It will be understood that the control device 10 may be integrated into the aforementioned intraoperative radiation therapy system as a software module stored in the memory 810, which may include computer instructions that may be executed by for example the processor 820 so as to perform the aforementioned operations. On the other hand, the control device 10 (including various modules and units therein) may also be implemented by dedicated hardware or firmware. It will be understood that all implementations of the control device 10, including software, hardware, firmware, or a combination thereof, fall within the scope of the present invention.

Referring to FIG. 4, the control device 10 may include an imaging control module 20, a modeling module 30, a radiation therapy volume determination module 40, a radiation therapy path planning module 50, and a radiation therapy execution module 60.

The imaging control module 20 may be used in the aforementioned imaging process. For example, the imaging control module 20 may plan an imaging scan path based on information of the auxiliary scanning component 100 and the imaging component 200, and control the robotic arm 300 to move the imaging component 200 along the planned scan path to scan the region of interest through the auxiliary scanning component 100, so as to acquire the plurality of images 500 of the region of interest. Then, the modeling module 30 may establish a 3D model of the region of interest based on the multiple images 500.

The radiation therapy volume determination module 40 may serve to determine the radiation therapy volume in the 3D model. Specifically, the radiation therapy volume determination module 40 may include an image recognition unit 42 and a radiation therapy volume selection unit 44. The image recognition unit 42 may automatically recognize a radiation therapy volume in the 3D model using image recognition technologies, and the radiation therapy volume selection unit 44 may receive a selection of the radiation therapy volume or a modification of the radiation therapy volume already recognized by the image recognition unit 42 from the user.

The radiation therapy path planning module 50 may serve to make a plan of a path along which the radiation therapy component scans the radiation therapy volume. Specifically, the radiation therapy path planning module 50 may include a sub-volume dividing unit 52, a radiation dose determining unit 54, and a radiation therapy path planning unit 56. The sub-volume dividing unit 52 may divide the determined radiation therapy volume into a number of sub-volumes, the radiation therapy dose determining unit 54 may determine the radiation dose for each sub-volume, and the radiation therapy path planning unit 56 may make a plan of the scan path and scan mode of the radiation therapy component scanning the sub-volumes in an intensity-modulated and energy-modulated manner. The scan mode may include a stepping scan mode and a dynamically continuous scan mode.

Although it is not shown, in some embodiments, the control device 10 may further include an evaluation module for evaluating the planned radiation therapy scan path. If the planned path meets requirements, for example, the possibility of potential damage to the normal tissues is low, the planned path may be used for subsequent radiation therapy. Otherwise, the path planning needs to be performed again.

Finally, the radiation therapy execution module 60 may control the robotic arm and the radiation therapy component to implement the radiation therapy according to the planned radiation therapy path. Specifically, the radiation therapy execution module 60 may include a robotic arm control unit 62 and a radiation therapy component control unit 64. The robotic arm control unit 62 may control the robotic arm 300 to move the radiation therapy component 600 or 700 along the planned path, and the radiation therapy component control unit 64 may control operation of the radiation therapy component 600 or 700 while it is moving, such as radiation intensity and energy of the radiation therapy component 600 or 700, so as to implement the intensity-modulated and energy-modulated radiation therapy.

The functions or operations of modules or units in the control device 10 have been briefly described above. It will be understood that these functions or operations have also been described in detail with reference to FIGS. 1-3. Therefore, further details of the functions or operations of each module or unit in the control device 10 may also be understood in connection with the description with reference to FIGS. 1-3.

In addition to the methods and apparatuses described above, aspects of the present invention may also be embodied as a computer program product that includes computer program instructions. The computer program instructions may, when executed by a processor, direct the intraoperative radiation therapy system of embodiments of the present invention to perform various operations, steps, and functions as described above. The computer program code may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Furthermore, aspects of the present invention may take the form of a computer readable medium having computer program instructions embodied thereon. The computer program instructions may, when executed by a processor, direct the intraoperative radiation therapy system of embodiments of the present invention to perform various operations, steps, and functions as described above. The computer readable medium may utilize any combination of one or more computer readable medium(s). The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing.

The features and advantages of the present invention may also be embodied in the following embodiments.

Embodiment 1, a method for planning a scan path for intraoperative radiation therapy comprising: acquiring a plurality of images of a region of interest through an auxiliary scanning component, establishing a 3D model of the region of interest based on the plurality of images of the region of interest, determining a radiation therapy volume based on the 3D model of the region of interest, and planning a scan path for a radiation therapy component to scan the radiation therapy volume.

Embodiment 2, the method of Embodiment 1 wherein the auxiliary scanning component comprises an applicator having an open upper end and a closed bottom, and the applicator is set up so that the closed bottom attaches to the region of interest.

Embodiment 3, the method of Embodiment 1 wherein acquiring a plurality of images of a region of interest through an auxiliary scanning component comprises using an ultrasonic device, a CT device, an X-ray device, or a MM device to acquire the plurality of images of the region of interest.

Embodiment 4, the method of Embodiment 1 wherein acquiring a plurality of images of a region of interest through an auxiliary scanning component comprises manipulating an ultrasonic device by a robotic arm to scan on the inner bottom surface of the auxiliary scanning component so as to acquire the plurality of images of the region of interest.

Embodiment 5, the method of Embodiment 1 wherein determining a radiation therapy volume based on the 3D model of the region of interest comprises recognizing the radiation therapy volume in the 3D model directly by an image recognition module, or receiving selection of the radiation therapy volume in the 3D model from a user, or preliminarily recognizing the radiation therapy volume in the 3D model by the image recognition module and then receiving modification of a user to the radiation therapy volume preliminarily recognized by the image recognition module so as to eventually determine the radiation therapy volume.

Embodiment 6, the method of Embodiment 1 wherein planning a scan path for a radiation therapy component to scan the radiation therapy volume comprises dividing the radiation therapy volume into a plurality of sub-volumes, determining a radiation dose for each of the sub-volumes, and planning a scan path and a scan mode for the radiation therapy component to scan each of the sub-volumes in an intensity-modulated and energy-modulated manner, and the scan mode includes a stepping scan mode and a dynamically continuous scan mode.

Embodiment 7, an intraoperative radiation therapy control device comprising an imaging control module for controlling an imaging component to move along a predetermined path and scan a region of interest through an auxiliary scanning component so as to acquire a plurality of images of the region of interest, a modeling module for establishing a 3D model of the region of interest based on the plurality of images of the region of interest, a radiation therapy volume determination module for determining a radiation therapy volume in the 3D model of the region of interest, and a radiation therapy path planning module for planning a path for a radiation therapy component to scan the radiation therapy volume.

Embodiment 8, the intraoperative radiation therapy control device of Embodiment 7 further comprising a radiation therapy execution module for controlling a robotic arm to move the radiation therapy component along the planned path to perform the radiation therapy.

Embodiment 9, the intraoperative radiation therapy control device of Embodiment 7 wherein the auxiliary scanning component comprises an applicator with an open upper end and a closed bottom, and the applicator is set up so that the closed bottom attaches to the region of interest.

Embodiment 10, the intraoperative radiation therapy control device of Embodiment 7 wherein the imaging control module controls an ultrasonic device, a CT device, an X-ray device, or a MM device to scan the region of interest so as to acquire the plurality of images of the region of interest.

Embodiment 11, the intraoperative radiation therapy control device of Embodiment 7 wherein the imaging component comprises an ultrasonic device, and the imaging control module controls a robotic arm to manipulate the ultrasonic device to scan the region of interest so as to acquire the plurality of images of the region of interest.

Embodiment 12, the intraoperative radiation therapy control device of Embodiment 11 wherein the imaging control module further plans the predetermined path based on information of the auxiliary scanning component and the ultrasonic device before it controls the robotic arm to manipulate the ultrasonic device.

Embodiment 13, the intraoperative radiation therapy control device of Embodiment 7 wherein the radiation therapy volume determination module comprises an image recognition unit to recognize the radiation therapy volume in the 3D model, and a radiation therapy volume selection unit to receive selection of the radiation therapy volume in the 3D model from a user.

Embodiment 14, the intraoperative radiation therapy control device of Embodiment 7 wherein the radiation therapy path planning module comprises a sub-volume dividing unit to divide the radiation therapy volume into a plurality of sub-volumes, a radiation dose determining unit to determine a radiation dose for each of the sub-volumes, and a radiation therapy path planning unit to plan a scan path and a scan mode for the radiation therapy component to scan each of the sub-volumes in an, intensity-modulated and energy-modulated manner, and the scan mode includes a stepping scan mode and a dynamically continuous scan mode.

Embodiment 15, the intraoperative radiation therapy control device of Embodiment 8 wherein the radiation therapy execution module comprises: a robotic arm control unit to control the robotic arm to move the radiation therapy component along the planned path to perform the radiation therapy, and a radiation therapy component control unit configured to control radiation intensity and energy of the radiation therapy component while the radiation therapy component is moving.

Embodiment 16, an intraoperative radiation therapy system comprising an auxiliary scanning component, an imaging component, a radiation therapy component, a robotic arm and a control component, the control component including a memory having computer instructions stored thereon and a processor configured to execute the computer instructions so as to perform the following steps: controlling the imaging component to scan a region of interest through the auxiliary scanning component placed on the region of interest to acquire a plurality of images of the region of interest, establishing a 3D model of the region of interest based on the plurality of images of the region of interest, determining a radiation therapy volume based on the 3D model, planning a path for the radiation therapy component to scan the radiation therapy volume, and controlling the robotic arm to move the radiation therapy component along the planned path to perform radiation therapy on the radiation therapy volume.

Embodiment 17, the intraoperative radiation therapy system of Embodiment 16 wherein the auxiliary scanning component comprises an applicator with an open upper end and a closed bottom, and the applicator is set up so that the closed bottom attaches to the region of interest.

Embodiment 18, the intraoperative radiation therapy system of Embodiment 16 wherein the imaging component comprises an ultrasonic device, a CT device, an X-ray device, or a MRI device.

Embodiment 19, the intraoperative radiation therapy system of Embodiment 18 wherein the imaging component comprises an ultrasonic device, and the ultrasonic device is moved by the robotic arm on the inner bottom surface of the auxiliary scanning component so as to acquire the plurality of images of the region of interest.

Embodiment 20, the intraoperative radiation therapy system of Embodiment 16 wherein determining a radiation therapy volume based on the 3D model comprises: recognizing the radiation therapy volume in the 3D model directly by image recognition; or receiving selection of the radiation therapy volume in the 3D model from a user; or preliminarily recognizing the radiation therapy volume in the 3D model by image recognition, and then receiving modification of the preliminarily recognized radiation therapy volume from the user so as to finally determine the radiation therapy volume.

Embodiment 21, the intraoperative radiation therapy system of Embodiment 16 wherein planning a path for the radiation therapy component to scan the radiation therapy volume comprises dividing the radiation therapy volume into a plurality of sub-volumes, determining a radiation dose for each of the sub-volumes, and planning a scan path and a scan mode for the radiation therapy component to scan each of the sub-volumes in an intensity-modulated and energy-modulated manner, and the scan mode includes a stepping scan mode and a dynamically continuous scan mode.

Embodiment 22, a computer-readable storage medium comprising computer program instructions stored thereon for performing the method of any one of Embodiments 1-6 as being executed in a processor.

Embodiment 23, the computer-readable storage medium of Embodiment 22 wherein the computer program instructions further, when executed in the processor, control the robotic arm to move the radiation therapy component along the planned path to perform radiation therapy on the radiation therapy volume.

Having described above several aspects of at least one embodiment, it is to be appreciated various alterations, modifications, and improvements will readily occur to those skilled in the art. Such alterations, modifications, and improvements are intended to be part of the disclosure and are intended to be within the scope of the invention. Accordingly, the foregoing description and drawings are by way of example only.

What is claimed and desired to be secured by Letters Patent of the United States is:

1. A method for intraoperative radiation therapy, comprising:

during surgery, acquiring a plurality of images of a region of interest through an applicator that has a cylinder shape with an open upper end and a closed bottom, wherein the applicator is placed on the region of interest so that the closed bottom attaches to the region of interest;

establishing a 3D model of the region of interest based on the plurality of images of the region of interest;

determining a radiation therapy volume for the intraoperative radiation therapy based on the 3D model of the region of interest; and planning a scan path for a radiation therapy component to scan the radiation therapy volume for the intraoperative radiation therapy, wherein acquiring the plurality of images of the region of interest through the applicator comprises moving an ultrasonic device by a robotic arm through the open upper end to attach to an inner surface of the closed bottom of the applicator, and manipulating the ultrasonic device by the robotic arm to scan on the inner surface of the closed bottom of the applicator so as to acquire the plurality of images of the region of interest, the ultrasonic device being installed at an end of the robotic arm, the method further comprising:

mounting an radiation therapy component on the robotic arm;

controlling the robotic arm to move the radiation therapy component along the planned path; and performing the intraoperative radiation therapy on the radiation therapy volume by the radiation therapy component mounted on the robotic arm while the radiation therapy component is moving, wherein the applicator remains placed on the region of interest while performing the intraoperative radiation therapy.

2. The method of claim 1, wherein determining the radiation therapy volume based on the 3D model of the region of interest comprises:

recognizing the radiation therapy volume in the 3D model directly by an image recognition module; or receiving selection of the radiation therapy volume in the 3D model from a user;

or preliminarily recognizing the radiation therapy volume in the 3D model by the image recognition module and then receiving modification of a user to the radiation therapy volume preliminarily recognized by the image recognition module so as to eventually determine the radiation therapy volume.

3. The method of claim 1, wherein planning the scan path for the radiation therapy component to scan the radiation therapy volume comprises:

dividing the radiation therapy volume into a plurality of sub-volumes;

determining a radiation dose for each of the plurality of sub-volumes; and for each of the plurality of sub-volumes, planning a scan path and a scan mode for the radiation therapy component to scan said each of the plurality of sub-volumes in an intensity-modulated and energy-modulated manner, wherein the scan mode includes a stepping scan mode and a dynamically continuous scan mode.

4. A system for intraoperative radiation therapy, comprising an applicator that has a cylinder shape with an open upper end and a closed bottom, a radiation therapy component, a robotic arm, an ultrasonic device installed at an end of the robotic arm, and a control component, the control component including a memory having computer instructions stored thereon and a processor configured to execute the computer instructions so as to perform the following steps:

moving the ultrasonic device by the robotic arm through the open upper end to attach to an inner surface of the closed bottom of the applicator placed on a region of interest;

controlling the ultrasonic device by the robotic arm to scan on the inner surface of the closed bottom of the applicator to acquire a plurality of images of the region of interest;

establishing a 3D model of the region of interest based on the plurality of images of the region of interest;

determining a radiation therapy volume based on the 3D model;

planning a path for the radiation therapy component to scan the radiation therapy volume;

controlling the robotic arm to move the radiation therapy component along the planned path after the radiation therapy component is mounted on the robotic arm; and performing the intraoperative radiation therapy on the radiation therapy volume by the radiation therapy component mounted on the robotic arm while the radiation therapy component is moving, wherein the applicator remains placed on the region of interest while performing the intraoperative radiation therapy.

5. The system of claim 4, wherein determining the radiation therapy volume based on the 3D model comprises:

recognizing the radiation therapy volume in the 3D model directly by image recognition; or receiving selection of the radiation therapy volume in the 3D model from a user; or preliminarily recognizing the radiation therapy volume in the 3D model by image recognition, and then receiving modification of the preliminarily recognized radiation therapy volume from the user so as to finally determine the radiation therapy volume.

6. The system of claim 4, wherein planning the path for the radiation therapy component to scan the radiation therapy volume comprises:

dividing the radiation therapy volume into a plurality of sub-volumes;

determining a radiation dose for each of the plurality of sub-volumes; and for each of the plurality of sub-volumes, planning a scan path and a scan mode for the radiation therapy component to scan said each of the plurality of sub-volumes in an intensity-modulated and energy-modulated manner, wherein the scan mode includes a stepping scan mode and a dynamically continuous scan mode.

* * * * *